US011755277B2

(12) United States Patent
Verbeke et al.

(10) Patent No.: US 11,755,277 B2
(45) Date of Patent: Sep. 12, 2023

(54) DAYDREAM-AWARE INFORMATION RECOVERY SYSTEM

(71) Applicant: HARMAN INTERNATIONAL INDUSTRIES, INCORPORATED, Stamford, CT (US)

(72) Inventors: Joseph Verbeke, San Francisco, CA (US); Stefan Marti, Oakland, CA (US)

(73) Assignee: Harman International Industries, Incorporated, Stamford, CT (US)

( * ) Notice: Subject to any disclaimer, the term of this patent is extended or adjusted under 35 U.S.C. 154(b) by 224 days.

(21) Appl. No.: 17/090,787

(22) Filed: Nov. 5, 2020

(65) Prior Publication Data

US 2022/0137915 A1    May 5, 2022

(51) Int. Cl.
*A61B 5/01* (2006.01)
*G06F 3/16* (2006.01)
(Continued)

(52) U.S. Cl.
CPC ............ *G06F 3/165* (2013.01); *A61B 5/0059* (2013.01); *A61B 5/01* (2013.01); *A61B 5/0531* (2013.01);
(Continued)

(58) Field of Classification Search
CPC ....... A61B 5/0059; A61B 5/01; A61B 5/0531; A61B 5/1126; A61B 5/16; A61B 5/163; A61B 5/165; A61B 5/369; A61B 5/6803; A61B 8/0808; A61B 2562/0219; A61B 5/486; A61B 5/6825; A61B 5/0006; A61B 5/020531; A61B 5/02055; A61B 5/4809; A61B 5/6831; A61B 5/6898; A61B 5/7246; A61B 5/7264; G06F 3/005; G06F 3/165; G06F 1/3212; G06F 3/011; G06F 3/016; G06F 9/451; G06F 16/3344; G06F 40/30; G06Q 10/087; G06Q 10/06; G06Q 10/103;
(Continued)

(56) References Cited

U.S. PATENT DOCUMENTS 6,545,682 B1 *   4/2003   Ventrella ................. G06F 3/011
                                                         345/473
7,617,094 B2 *   11/2009  Aoki ....................... G10L 17/00
                                                         704/214
(Continued)

FOREIGN PATENT DOCUMENTS

EP         2 200 347 A2      6/2010

OTHER PUBLICATIONS

Shi et al., "Galvanic Skin Response (GSR) as an Index of Cognitive Load", CHI 2007, Apr. 28-May 3, 2007, San Jose, California, USA, 6 pages.

(Continued)

*Primary Examiner* — Gerald Gauthier
(74) *Attorney, Agent, or Firm* — Artegis Law Group, LLP (57) ABSTRACT

A system includes a sensing module configured to collect physiological information from a user; an audio input device configured to capture auditory content that is in an environment proximate the user; and one or more processors configured to: determine that a user has entered a state of inwardly focused attention based on first physiological information collected from the user; and in response, record the auditory content captured by the audio input device.

19 Claims, 6 Drawing Sheets

(51) Int. Cl.

| | |
|---|---|
| *A61B 5/16* | (2006.01) |
| *A61B 5/369* | (2021.01) |
| *A61B 5/00* | (2006.01) |
| *A61B 5/0531* | (2021.01) |
| *A61B 5/11* | (2006.01) |
| *G10L 15/22* | (2006.01) |
| *G10L 15/26* | (2006.01) |
| *G10L 21/043* | (2013.01) |
| *G10L 25/51* | (2013.01) |
| *G10L 25/78* | (2013.01) |
| *H04R 1/10* | (2006.01) |

(52) U.S. Cl.
CPC ............ *A61B 5/1126* (2013.01); *A61B 5/163* (2017.08); *A61B 5/165* (2013.01); *A61B 5/369* (2021.01); *A61B 5/6803* (2013.01); *G10L 15/22* (2013.01); *G10L 15/26* (2013.01); *G10L 21/043* (2013.01); *G10L 25/51* (2013.01); *G10L 25/78* (2013.01); *A61B 2562/0219* (2013.01); *H04R 1/1008* (2013.01); *H04R 1/1016* (2013.01); *H04R 1/1041* (2013.01)

(58) Field of Classification Search
CPC ......... G06Q 50/01; G10L 15/22; G10L 15/26; G10L 17/00; G10L 21/043; G10L 25/51; G10L 25/78; H04N 5/23222; H04N 21/4307; H04N 13/20; H04R 1/1008; H04R 1/1016; H04R 1/1041; H04R 1/105; H04R 25/70; A61J 17/103; A61K 31/404; A61K 31/47; A61P 25/08; A61P 25/16; E03C 1/0408; E03C 1/057; G06V 40/197; G06V 20/588; G06V 40/10; G06V 40/20; G07F 17/3239; G09B 19/00; G16H 20/70; A63F 13/77; G02B 27/017; G05D 1/0214; G06N 5/02; G06N 20/00; G06T 7/70; G06T 19/20; H05B 45/10
See application file for complete search history.

(56) References Cited

U.S. PATENT DOCUMENTS

| | | | | |
|---|---|---|---|---|
| 9,579,060 | B1* | 2/2017 | Lisy ...................... | A61B 5/165 |
| 9,811,991 | B2 | 11/2017 | Di Censo et al. | |
| 9,876,985 | B2* | 1/2018 | Di Censo ................ | G06F 3/005 |
| 10,205,988 | B1 | 2/2019 | Waterman et al. | |
| 10,362,385 | B1 | 7/2019 | Di Censo et al. | |
| 10,762,928 | B1 | 9/2020 | Camus et al. | |
| 11,559,255 | B1* | 1/2023 | Lisy ...................... | A61B 5/7203 |
| 11,620,916 | B1* | 4/2023 | Sastry .................... | G06F 40/30 |
| | | | | 434/367 |
| 2002/0154787 | A1* | 10/2002 | Rice ..................... | H04R 29/008 |
| | | | | 381/124 |
| 2004/0183749 | A1 | 9/2004 | Vertegaal | |
| 2006/0029198 | A1* | 2/2006 | Dorneich ............ | A61B 5/0006 |
| | | | | 379/88.22 |
| 2006/0281543 | A1* | 12/2006 | Sutton ................ | G07F 17/3239 |
| | | | | 463/29 |
| 2008/0269629 | A1* | 10/2008 | Reiner ................ | A61B 5/6831 |
| | | | | 600/544 |
| 2012/0259803 | A1* | 10/2012 | Whitlow ............. | A61B 5/7264 |
| | | | | 706/20 |
| 2014/0108309 | A1* | 4/2014 | Frank .................... | G06Q 50/01 |
| | | | | 706/12 |
| 2014/0108842 | A1* | 4/2014 | Frank .................... | G06F 1/3212 |
| | | | | 713/323 |
| 2014/0149177 | A1* | 5/2014 | Frank .................... | G06Q 10/06 |
| | | | | 705/7.29 |
| 2015/0223731 | A1* | 8/2015 | Sahin ...................... | A61B 5/16 |
| | | | | 600/595 |
| 2015/0281824 | A1 | 10/2015 | Nguyen et al. | |
| 2015/0356836 | A1* | 12/2015 | Schlesinger ........... | H04R 1/105 |
| | | | | 704/235 |
| 2016/0005320 | A1* | 1/2016 | deCharms ............ | A61B 8/0808 |
| | | | | 434/236 |
| 2016/0128617 | A1* | 5/2016 | Morris ................. | G06Q 10/103 |
| | | | | 434/236 |
| 2017/0006214 | A1* | 1/2017 | Andreassen ........ | H04N 5/23222 |
| 2017/0223413 | A1 | 8/2017 | Kozloski et al. | |
| 2017/0251295 | A1* | 8/2017 | Pergament ........... | H04R 1/1041 |
| 2017/0255814 | A1* | 9/2017 | Kaehler ............... | G06V 40/197 |
| 2017/0339338 | A1* | 11/2017 | Gordon ................ | H04N 5/77 |
| 2017/0354326 | A1* | 12/2017 | Pugh .................... | A61B 5/7246 |
| 2018/0101989 | A1* | 4/2018 | Frueh .................... | G06T 19/20 |
| 2018/0286268 | A1* | 10/2018 | Ni ........................ | G02B 27/017 |
| 2019/0043214 | A1* | 2/2019 | Chilcote-Bacco ........ | G06T 7/70 |
| 2019/0056731 | A1* | 2/2019 | Westbrook ........... | G05D 1/0214 |
| 2019/0101977 | A1* | 4/2019 | Armstrong-Muntner .................... G06N 20/00 |
| 2019/0320963 | A1* | 10/2019 | Komura ................. | G10L 25/51 |
| 2019/0332669 | A1* | 10/2019 | Lewis .................. | G06F 16/3344 |
| 2020/0023157 | A1* | 1/2020 | Lewis .................. | A61B 5/6803 |
| 2020/0067998 | A1* | 2/2020 | Pilnock .................. | A63F 13/77 |
| 2020/0100692 | A1* | 4/2020 | Cotton ................ | A61B 5/6898 |
| 2020/0159774 | A1* | 5/2020 | Di Cairano-Gilfedder ................ G06N 5/02 |
| 2020/0245068 | A1* | 7/2020 | Shah ...................... | G06N 20/00 |
| 2020/0267949 | A1* | 8/2020 | Bagnall .................. | H05B 45/10 |
| 2020/0288262 | A1* | 9/2020 | Eronen ................. | G10L 25/48 |
| 2020/0310117 | A1* | 10/2020 | Qian .................... | G02B 27/017 |
| 2021/0403022 | A1* | 12/2021 | Hong ...................... | G06V 40/20 |
| 2022/0121867 | A1* | 4/2022 | Arar ................... | G06V 20/588 |
| 2022/0132194 | A1* | 4/2022 | Aimone ............. | H04N 21/4307 |
| 2022/0137915 | A1* | 5/2022 | Verbeke ................. | G10L 25/51 |
| | | | | 704/235 |
| 2022/0245574 | A1* | 8/2022 | Cella ................... | G06Q 10/087 |

OTHER PUBLICATIONS

Antrobus et al., "Eye Movements Accompanying Daydreaming, Visual Imagery, and Though Suppression", Journal of Abnormal and Social Psychology, 1964, vol. 69, No. 3, 244-252, 9 pages.

Cinaz et al., "Monitoring of Mental Workload Levels", IADIS International Conference e-Health 2010, 5 pages.

Grassmann et al., "Respiratory Changes in Response to Cognitive Load: A Systematic Review", Hindawi Publishing Corporation, Neural Plasticity, vol. 2016, Article ID 8146809, http://dx.doi.org/101155/2016/8146809, 17 pages.

Braboszcz et al., "Lost in thoughts: Nerual markers of low alertness during mind wandering", Article in Neuroimage—Oct. 2010, DOI: 10.1016/j.neuroimage.2010.10.008 Source: PubMed, 31 pages.

U.S. patent application entitled, "Modifying Media Content Playback Based on User Mental State", U.S. Appl. No. 16/907,096, filed Jun. 19, 2020, 54 pages.

Huang et al., "Moment-to-Moment Detection of Internal Thought during Video Viewing from Eye Vergence Behavior", MM '19, Oct. 21-25, 2019, Nice, France, DOI: https://doi.org/10.1145/3343031.3350573, 9 pages.

* cited by examiner

DAYDREAM-AWARE INFORMATION RECOVERY SYSTEM

BACKGROUND

Field of the Embodiments

Embodiments of the present disclosure relate generally to psychophysiological systems and, more specifically, to a daydream-aware information recovery system.

Description of the Related Art

Daydreaming, which is a mental state in which the attention of a person is inwardly focused, can occur frequently in daily life. Typically, the train of thought of a daydreamer detaches from external tasks and stimuli and drifts to subjects that may be disconnected from the daydreamers current surroundings, such as past experiences and future events.

In addition to occurring frequently in most persons, daydreaming is known to have numerous benefits. For example, the mind of a daydreamer travels through various areas of the memory, subconsciously collecting pieces of information that can then be connected. Because such connections often manifest as new and creative ideas, daydreaming is associated with enhanced creativity. Also, some studies show daydreaming to be linked to improvements in working memory, which is the ability of the brain to store and then recall information in the presence of distractions (e.g., Levinson, D. B., Smallwood, J., Davidson, R. J., Psychol Sci. 2012 April; 23(4): 375-80. The Persistence of Thought: Evidence for a Role of Working Memory in the Maintenance of Task-Unrelated Thinking). Daydreaming is further linked in many studies to improved mental performance and productivity and to reduced levels of stress. Thus, in daily life, periods of daydreaming may not only be pleasant, but intellectually productive and mentally therapeutic.

However, when a person enters a daydreaming state, by definition that person no longer has a significant level of attention directed to his or her surroundings. Thus, the daydreamer typically cannot retain information pertaining to experiences and events that take place during the daydreaming session. As a result, there is a trade-off between the ability for a person to experience some level of daydreaming and the ability for the person to experience and remember events associated with the surrounding environment while the person is daydreaming.

As the foregoing illustrates, improved techniques for enabling a person to daydream without missing events that occur during the daydream would be useful.

SUMMARY

The various embodiments set forth a system for recording auditory content while a user is in a daydreaming state. The system includes a sensing module configured to collect physiological information from a user; an audio input device configured to capture auditory content that is in an environment proximate the user; and one or more processors configured to: determine that a user has entered a state of inwardly focused attention based on first physiological information collected from the user; and in response, record the auditory content captured by the audio input device.

At least one technological improvement of the disclosed embodiments is that a user is free to enjoy the benefits of having a daydream session or other spontaneous, self-directed thoughts and associations without missing external auditory experiences or content that is audible to the user during the daydream session. Another technological improvement of the disclosed embodiments is that such external auditory experiences and/or content can be provided to the user in a different modality and/or played back at a more convenient speed. These technical advantages provide one or more technological advancements over prior art approaches.

BRIEF DESCRIPTION OF THE SEVERAL VIEWS OF THE DRAWINGS

So that the manner in which the above recited features of the one or more embodiments can be understood in detail, a more particular description of the one or more embodiments, briefly summarized above, may be had by reference to certain specific embodiments, some of which are illustrated in the appended drawings. It is to be noted, however, that the appended drawings illustrate only typical embodiments and are therefore not to be considered limiting of its scope in any manner, for the scope of the various embodiments subsumes other embodiments as well.

For clarity, identical reference numbers have been used, where applicable, to designate identical elements that are common between figures. It is contemplated that features of one embodiment may be incorporated in other embodiments without further recitation.

DETAILED DESCRIPTION

Figure 1:
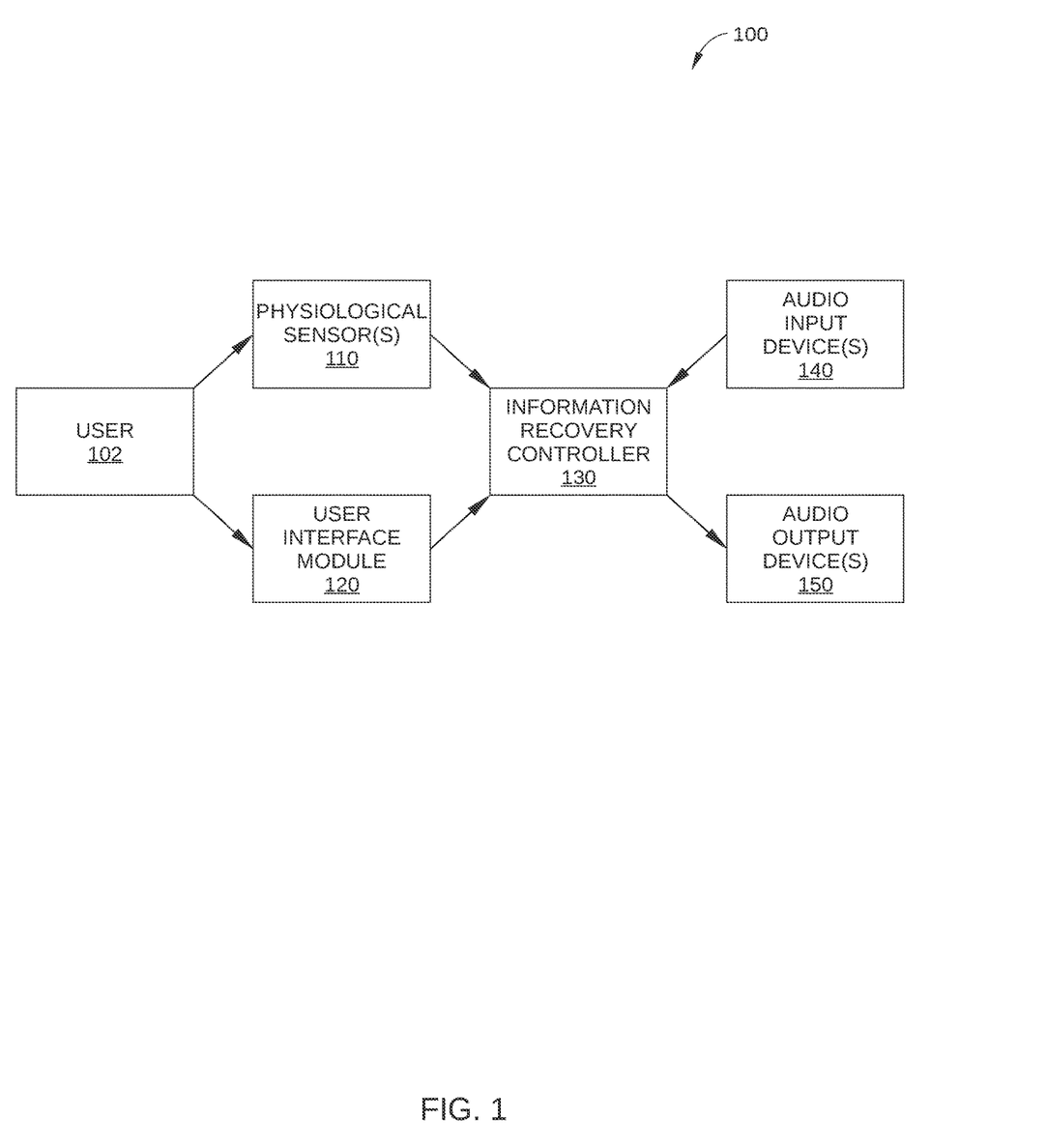
FIG. 1 is a block diagram illustrating a daydream-aware information recovery system configured to implement one or more embodiments.

FIG. 1 is a block diagram illustrating a daydream-aware information recovery system 100 configured to implement one or more embodiments. Daydream-aware information recovery system 100 is configured to determine that a user has entered a daydreaming state, capture auditory content from the surroundings of the user, and provide the captured auditory content to the user at a suitable time. In some embodiments, daydream-aware information recovery system 100 is configured to provide the captured auditory content once the user has exited the daydreaming state, and in other embodiments daydream-aware information recovery system 100 is configured to provide the captured auditory content at a later, user-selected time. In some embodiments, daydream-aware information recovery system 100 is configured to capture the auditory content via an audio recording that is subsequently provided to the user via audio playback. Alternatively or additionally, in some embodiments, daydream-aware information recovery system 100 is configured to capture the auditory content via an audio recording, change the auditory content to a different modality (e.g., a text-based message), then provide the auditory content in the different modality to the user. In such embodiments, the auditory content may be provided to the user in the different modality immediately after daydreaming has ceased and/or at a user-selected time. Further, in such embodiments, daydream-aware information recovery system 100 may be configured to create a log of the different modality content for subsequent consumption by the user. In the embodiment illustrated in FIG. 1, daydream-aware information recovery system 100 includes one or more physiological sensors 110, a user interface module 120, an information recovery controller 130, one or more audio input devices 140, and one or more audio output devices 150.

Physiological sensors 110 are configured to receive or otherwise monitor physiological information from a user 102, where such physiological information enables detection of a daydream state in user 102. Physiological sensors 110 can include one or more sensing devices for the detection of one or more types of physiological information associated with user 102.

In some embodiments, physiological sensors 110 include sensors for electroencephalography (EEG), which can measure electrical activity in the brain of user 102, for example in the form of brain wave patterns. In such embodiments, physiological sensors 110 include two or more EEG sensors that are configured to contact a surface of a head of user 102 and a sensor that is coupled to an electrical ground, such as another surface of the body of user 102. In such embodiments, daydream-aware information recovery system 100 includes at least one EEG sensor that is configured to contact a first surface of the head of user 102 on a first hemisphere of the head (for example the left half of the head) and at least one EEG sensor that is configured to contact a second surface of the head of user 102 on a second hemisphere of the head (for example the right half of the head). Generally, more EEG sensors provide more accurate EEG information. Thus, in some embodiments, daydream-aware information recovery system 100 includes a plurality of EEG sensors, where a first portion of the plurality of EEG sensors are configured to contact surfaces on the first hemisphere of the head and a second portion of the plurality of EEG sensors are configured to contact surfaces on the second hemisphere of the head.

In some embodiments, physiological sensors 110 include sensors for electrodermal activity. In such embodiments, physiological sensors 110 include at least one sensor that is configured to contact a surface of a body part of user 102 (such as a surface of the face, neck, ear, arm, hand, and/or the like) and measure skin conductance and/or skin temperature. In some embodiments, physiological sensors 110 include one or more sensors for enabling camera-based pupillometry by imaging pupil size of user 102 over time. In such embodiments, physiological sensors 110 include one or more cameras directed toward one or both eyes of user 102, where such cameras are configured to record a current size of one or both pupils of user 102. In some embodiments, physiological sensors 110 include one or more sensors for performing reflective photosensing of one or more physiological metrics of user 102. In such embodiments, physiological sensors 110 include one or more sensors that are configured to be positioned on at least one surface of the body of user 102. Measurements performed by such sensors, such as measurements of blood vessels, enable determination of pulse rate, breathing rate, and blood oxygen saturation level, among other physiological measurements.

In some embodiments, physiological sensors 110 include one or more inertial measurement unit (IMU) sensors for analyzing the movements of user 102. In such embodiments, physiological sensors 110 include one or more sensors configured to enable the determination of the breathing rate of user 102. For example, an IMU can be employed to determine the breathing rate of user 102 by detecting the small and/or micro cyclical movements associated with respiration. Alternatively or additionally, in some embodiments, the output of an IMU can indicate macro movements that can be employed by a suitable algorithm or machine learning module to determine whether user 102 has stopped moving or become substantially motionless. In such embodiments, such a determination may be included as an input indicated that user 102 may have entered a daydreaming state.

In some embodiments, one or more of the sensors included in physiological sensors 110 are incorporated in a head-worn device or wearable computing device, such as an audio headphone apparatus, a smart headphone system, an audio earpiece/earbud or a pair of audio earpieces/earbuds, a smart ear piece, a pair of smart glasses, and/or the like. Examples of such embodiments are described below in greater detail in conjunction with FIGS. 3 and 4.

User interface module 120 is configured to receive user inputs for controlling certain operations of daydream-aware information recovery system 100 and transmitting such inputs to information recovery controller 130. Thus, user interface module 120 enables user 102 to control certain operations of daydream-aware information recovery system 100. Examples of such operations include powering on and powering off, beginning monitoring for a dream state in user 102, beginning playback of information recording during a particular dream state of user 102, selecting a modality of such information when provided by daydream-aware information recovery system 100 to user 102, and/or the like.

In some embodiments, user interface module 120 includes one or more physical buttons or switches, which may be, for example, incorporated into a head-worn device that includes one or more physiological sensors 110. In some embodiments, user interface module 120 includes a gestural interface, such as one or more inertial measurement unit (IMU) for detecting a tap by user 102, one or more resistive and/or capacitive sensors for detecting a touch by user 102, one or more force sensors for detecting other gestures or selections by user 102, and/or the like. In some embodiments, user interface module 120 includes a wireless interface that is configured to connect to a computing device associated with user 102, such as a smartphone, electronic tablet, laptop computer, smartwatch, and/or the like. In such embodiments, the wireless interface is further configured to communicate with a control application executing on such a computing device, so that user 102 can provide inputs to daydream-aware information recovery system 100 via the computing device. In some embodiments, user interface module 120 includes a voice control system that is configured to interpret voice commands from user 102 and communicate such commands to the control application executing on the computing device.

Audio input devices 140 include one or more microphones configured to receive auditory content that is in an environment surrounding or proximate to user 102. Thus, sounds and/or speech that is audible to user 102 can be captured (e.g., received and/or detected) by one or more of audio input devices 140 when user 102 is determined to be in a daydream state. In some embodiments, audio input devices 140 include an array of multiple microphones that are configured to receive auditory content from multiple directions around user 102. In some embodiments, auditory content can be captured omnidirectionally around user 102.

In some embodiments, one or more audio devices 140 are incorporated in a head-worn device or wearable computing device. Alternatively or additionally, in some embodiments, one or more audio devices 140 of daydream-aware information recovery system 100 are not implemented as a physical microphone a head-worn or wearable computing device. In such embodiments, an audio stream from an audio device external to a head-worn or wearable computing device is employed to receive auditory content that is in an environment surrounding or proximate to user 102. For example, in such embodiments, an audio stream captured from a conference call session and/or from a phone call is received by daydream-aware information recovery system 100 when user 102 is determined to be in a daydream state. Thus, when a user attends a conference call or phone call and enters a daydream state, daydream-aware information recovery system 100 records audio from the conference call system (e.g., from a traditional conference call desktop appliance, a computing device running a video conference application, from the telephone or smartphone performing the call, and/or the like). Thus, in such embodiments, an audio input stream is generated by one or more audio devices 140 that are not included in the head-worn or wearable computing device that includes daydream-aware information recovery system 100.

Audio output devices 150 include one or more loudspeakers configured to provide auditory content to user 102, such as sounds and/or speech that is audible to user 102 during the daydreaming state and has been captured by audio input devices 140. Such auditory content can be played back to user 102 via audio output devices 150 once user 102 has been determined to exit the daydream state. In some embodiments, audio output devices 150 are configured to provide such auditory content as private auditory content, which is not audible to other persons near user 102. In such embodiments, audio output devices 150 are incorporated into a head-worn audio device or head-worn smart device, such as a headphone apparatus or an earpiece apparatus.

Information recovery controller 130 is configured to control various operations and functions of daydream-aware information recovery system 100. Such operations and functions include one or more of: receiving physiological information from physiological sensors 110; determining that user 102 has entered a daydream state based on such physiological information; receiving auditory content from audio input devices 140; determining that speech is audible to user 102 while user 102 is in the daydreaming state; performing audio processing on auditory content received from audio input devices 140 (e.g., speech clarification); performing a speech-to-text-operation on at least a portion of the auditory content received from audio input devices 140; transmitting certain auditory content to audio output devices 150 for playback to user 102; performing audio processing on such auditory content transmitted to audio output devices 150 (e.g., playback speed acceleration); performing a text-to-speech operation on at least a portion of text generated based on the auditory content received from audio input devices 140; and/or receiving user inputs via user interface module 120 and responding thereto. One embodiment of information recovery controller 130 is described below in conjunction with FIG. 2.

Figure 2:
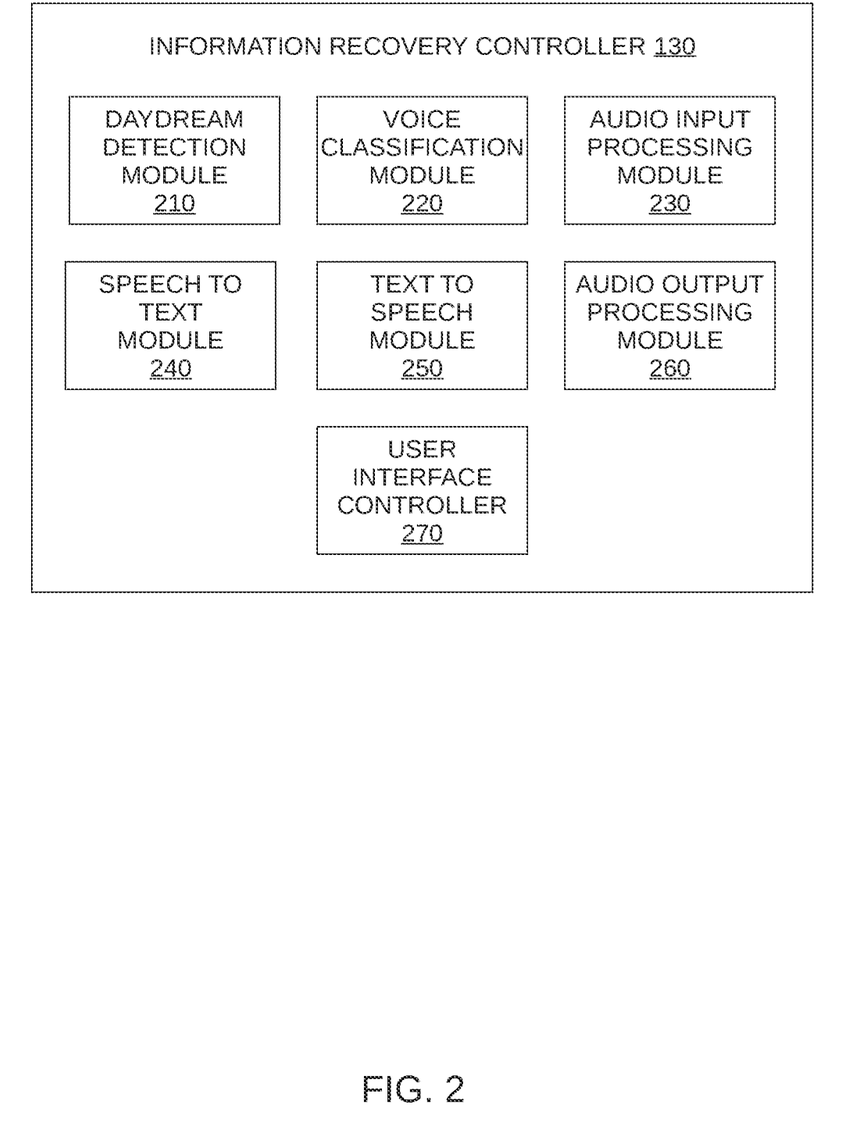
FIG. 2 is a block diagram of an information recovery controller in the daydream-aware information recovery system of FIG. 1, according to one or more embodiments.

FIG. 2 is a block diagram of information recovery controller 130, according to one or more embodiments. As shown, information recovery controller 130 includes one or more of the following components: a daydream detection module 210, a voice classification module 220, an audio input processing module 230, a speech-to-text module 240, a text-to-speech module 250, an audio output processing module 260, and/or a user interface controller 270. In the following description, certain functions of information recovery controller 130 are divided between the above components. In other embodiments, the functionality of one or more of the above-components is combined into a single device or module.

Daydream detection module 210 is configured to determine when user 102 has entered and/or exited a daydream state based on physiological information received from physiological sensors 110 in the form of one or more sensor outputs. In some embodiments, the sensor output(s) received from physiological sensors 110 is raw (e.g., not pre-processed) sensor information. In some embodiments, one or more of physiological sensors 110 are configured to provide pre-processed data, such as data including an indication that a threshold value has been crossed or a specific state has been detected.

In some embodiments, daydream detection module 210 is configured to determine that user 102 has entered or exited a daydreaming state when a specific event or combination of events has occurred as indicated by the sensor output(s) received from physiological sensors 110. Examples of such events include a threshold value being crossed, such as a threshold value of a change in skin conductance of user 102, or a specific state being detected, such as detection of a specific EEG brainwave pattern of user 102. Thus, in such embodiments, an output from daydream detection module 210 may include a Boolean variable value indicating whether user 102 is currently in a daydreaming state or not in a daydreaming state.

In some embodiments, daydream detection module 210 is configured to determine that user 102 has entered a daydreaming state by employing and/or including a machine learning classifier algorithm. In such embodiments, the machine learning classifier algorithm is programmed or trained to classify (e.g., determine) that user 102 is in a daydreaming state based on the sensor output(s) received from physiological sensors 110. In such embodiments, the machine learning classifier algorithm is previously trained from a data set correlating the specific type or types of sensor output(s) received from physiological sensors 110 to a neurological state of daydreaming. As a result, based on a specific set of sensor output(s) from physiological sensors 110, the machine learning classifier algorithm can determine a probability that user 102 is currently in a daydreaming state. Based on such a probability, daydream detection module 210 determines whether user 102 is in a daydreaming state. In such embodiments, an output from daydream detection module 210 may include a Boolean variable value indicating whether user 102 is currently in a daydreaming state or not in a daydreaming state.

In some embodiments, the training data set can be a generic data set generated based on a large number of users. In some embodiments, the training data set can be a user-specific data set generated based on one or more training sessions using data for user 102. In some embodiments, the training data set can be a combination of generic data and user-specific data.

Voice classification module 220 is configured to determine that speech is audible to user 102 while user 102 is in a daydreaming state. In some embodiments, voice classification module 220 is configured to determine such speech based on auditory content received from audio input device(s) 140 during the current daydreaming session experienced by user 102. In some embodiments, voice classification module 220 includes a machine-learning classifier algorithm trained to detect speech in the auditory content received from audio input device(s) 140. In some embodiments, when voice classification module 220 detects speech while user 102 is in a daydreaming state, information recovery controller 130 captures, records, and in some embodiments modifies the auditory content received from audio input device(s) 140 during the current daydreaming session experienced by user 102.

Audio input processing module 230 is configured to perform audio processing on auditory content received from audio input device(s) 140, such as speech clarification. Such audio processing facilitates generation of text by speech-to-text module 240 from the auditory content received from audio input device(s) 140.

Speech-to-text module 240 is configured to perform a speech-to-text-operation on at least a portion of the auditory content received from audio input devices 140. In embodiments in which speech-to-text module 240 is employed, the text generated by speech-to-text module 240 is stored for provision to user 102 after the current daydreaming session. In some embodiments, information recovery controller 130 provides such text to user 102 via audio output devices 150 as synthesized speech. Alternatively or additionally, in some embodiments, information recovery controller 130 provides such text to user 102 as text-based information, such as a text file or text-based message for transmission to a computing device associated with user 102. Thus, in such embodiments, information recovery controller 130 changes the auditory content received from audio input device(s) 140 to a different modality of content. Further, in some embodiments, the text-based information provided by information recovery controller 130 may include a verbatim or near-verbatim transcript of some or all of the auditory content received from audio input devices 140. Alternatively or additionally, in some embodiments, the text-based information provided by information recovery controller 130 may include summarized text associated with some or all of the auditory content received from audio input devices 140. In such embodiments, speech-to-text module 240 may include one or more algorithms and/or methods for text summarization known in the art.

Text-to-speech module 250 is configured to perform a text-to-speech operation on at least a portion of text generated based on the auditory content received from audio input device(s) 140. Text-to-speech module 250 employs such text as input to a text-to-speech voice synthesizer to generate audio for playback to user 102 by audio output device(s) 150. In embodiments in which text-to-speech module 250 is employed, the audio file can be stored prior to being provided to user 102 after the current daydreaming session.

Audio output processing module 260 is configured to perform audio processing on auditory content prior to being transmitted to audio output devices 150. In some embodiments, such audio processing includes determining a playback speed of the auditory content transmitted to audio output devices 150. In some embodiments, audio output processing module 260 determines the playback speed based on one or more factors. Examples of such factors include a user preference for playback speed associated with user 102, a playback speed associated with a user input received via user interface module 120, and a duration of a time interval. In some embodiments, the playback speed is based on a time interval associated with the current daydream session experienced by user 102. In some embodiments, the playback speed is based on a time interval during which auditory content is recorded, such as a duration of a particular daydreaming session.

In some embodiments, audio output processing module 260 is configured to increase playback speed of an audio file that is played back to user 102 after the current daydreaming session ends. Consequently, user 102 can listen to a representation (such as an audio file) of missed auditory content in a time interval having a shorter duration than the duration of the just-completed daydreaming session. In some embodiments, audio output processing module 260 is configured to increase playback speed of the audio file played back to user 102 based on the duration of the just-completed daydreaming session. Thus, in such embodiments, user 102 can review missed auditory content relatively quickly, even though a particular daydream session may have a relatively long duration. Alternatively or additionally, in some embodiments, audio output processing module 260 is configured to increase playback speed of such an audio file based on a user preference for playback speed associated with user 102 or on a user input received via user interface module 120. Thus, in such embodiments, user 102 can review missed auditory content at an increased speed that user 102 selects or is comfortable with.

In some embodiments, the audio processing performed on auditory content by audio output processing module 260 includes cancellation of one or more voices external to auditory content, such as voices present in the environment surrounding or proximate to user 102. For example, in such embodiments, audio output processing module 260 may include a voice cancellation algorithm Thus, in such embodiments, user 102 can listen to the representation of the missed auditory content without being distracted by voices and/or conversation in the environment surrounding or proximate to user 102.

User interface controller 270 is configured to receive user inputs via user interface module 120 and respond thereto. Depending on the configuration of user interface module 120, such user inputs can include one or more of physical inputs via buttons or switches, voice commands received by audio input device(s) 140, gestures received via a touch screen, finger taps received by an IMU, and/or the like. Based on such user inputs, user interface controller 270 causes certain functions or operations of daydream-aware information recovery system 100 to start, stop, and/or change. Examples of such operations or functions include powering on and powering off, beginning monitoring for a dream state in user 102, beginning playback of information recorded during a particular dream state of user 102, selecting a modality of such information when provided to user 102, and/or the like.

In addition to the above functionalities, in some embodiments information recovery controller 130 is further configured to record auditory content after a particular daydream session. That is, after determining that user 102 has exited a particular daydream session, information recovery controller 130 continues to record auditory content that is audible to user 102. Thus, while a representation of auditory content missed by user 102 is provided to user 102, additional auditory content is captured and subsequently provided to user 102 so that user 102 can listen to all the auditory content at an increased speed until user 102 catches up to the auditory content of the present time. In such embodiments, the modality of the auditory content captured after the particular daydream session can be modified and/or the playback speed increased in the same way described above for the auditory content missed during the daydream session.

In some embodiments, one or more of the sensors included in physiological sensors 110 are incorporated in a head-worn device or wearable computing device. One such embodiment is illustrated in FIG. 3, and another such embodiment is illustrated in FIG. 4.

Figure 3:
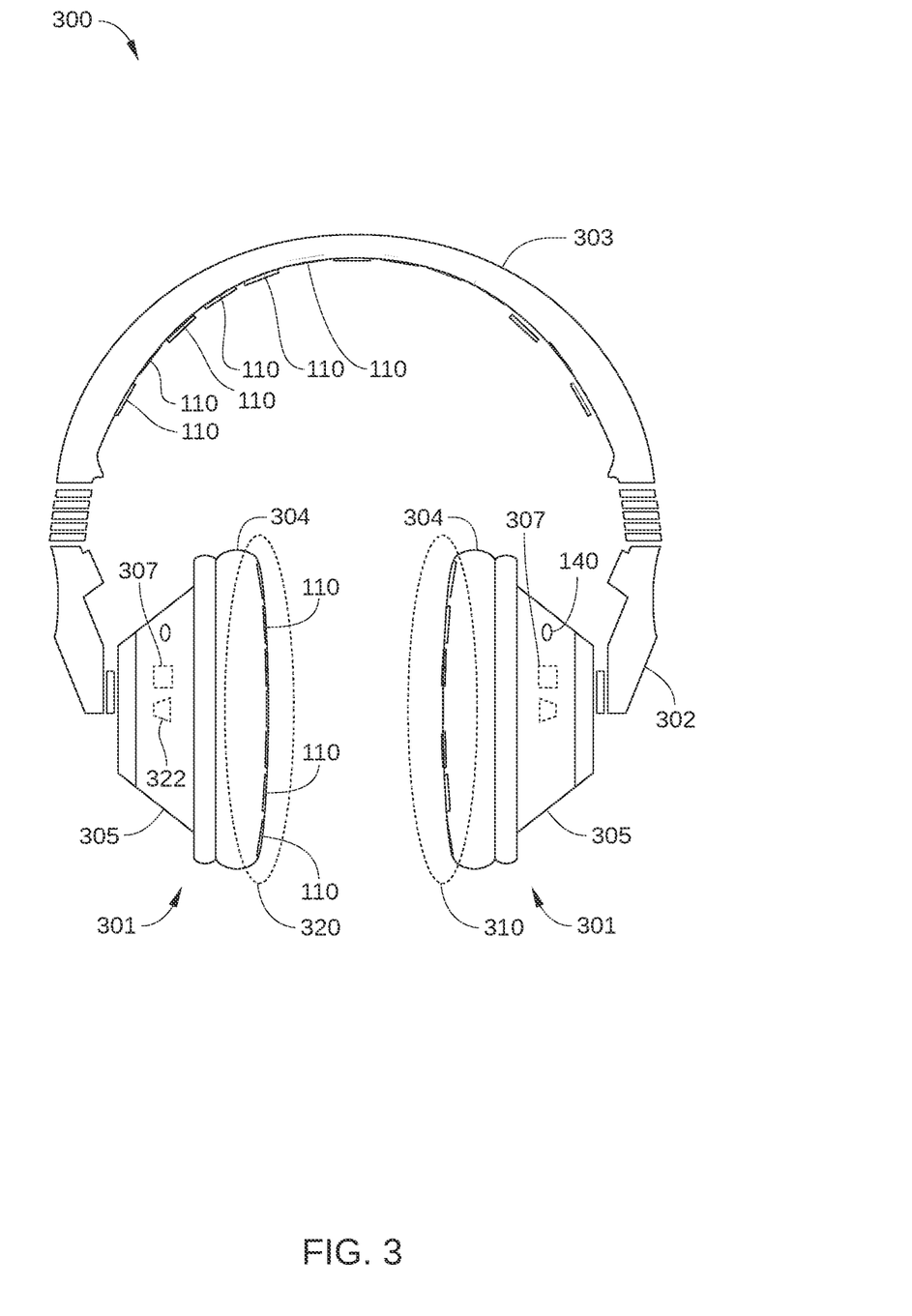
FIG. 3 is a schematic diagram illustrating a headphone system that includes a daydream-aware information recovery system, according to one or more aspects of the present disclosure.
Figure 4:
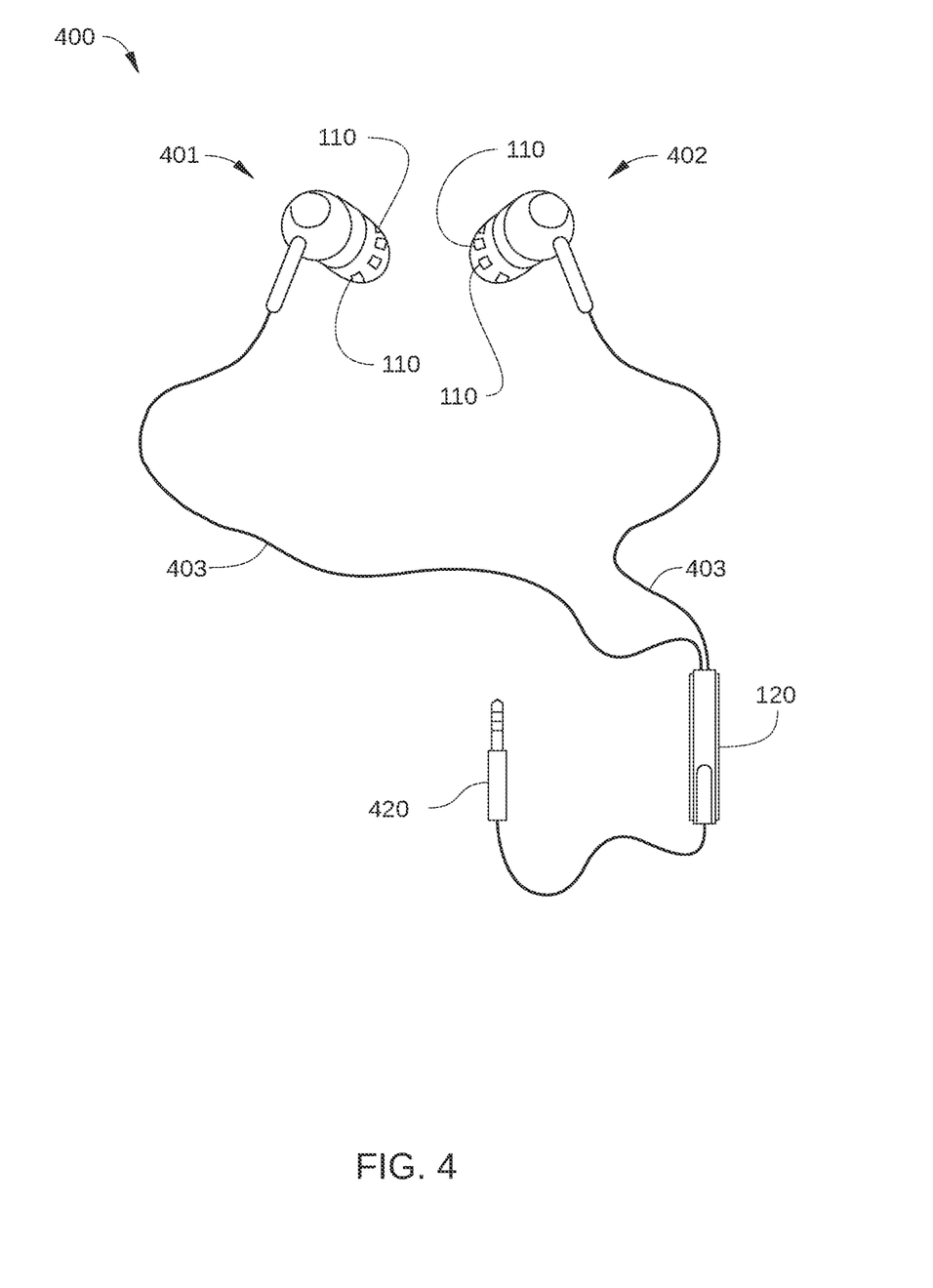
FIG. 4 is a schematic diagram illustrating an ear-mounted device that includes a daydream-aware information recovery system, according to various embodiments.

FIG. 3 is a schematic diagram illustrating a headphone system 300 that includes daydream-aware information recovery system 100, according to one or more aspects of the present disclosure. Headphone system 300 may include, without limitation, two earcups 301 coupled to a headband 303 via a respective arm 302. In the embodiment shown in FIG. 3, headphone system 300 is configured as a circumaural headphone system, where each earcup 301 is configured to fit over the outer ear of a user. In alternative embodiments, headphone system 300 is configured as a supra-aural headphone system, where each earcup 301 is configured to fit against the outer ear of a user. In some embodiments, headphone system 300 may be configured with a single earcup 301 rather than two earcups 301.

In some embodiments, each earcup 301 includes, among other things, a loudspeaker 322, an ear-surround cushion 304 coupled to a housing 305, one or more physiological sensors 110, and, in some embodiments, an IMU 307 is disposed within one or both earcups 301. In other embodiments, one or more IMUs 307 may be disposed within headband 303. In some embodiments, one or more physiological sensors 110 are also disposed on headband 303. As shown, the one or more physiological sensors 110 incorporated into headphone system 300 are each positioned to make contact with a different portion of a surface of a head (not shown) of a user. That is, when headphone system 300 is worn by a user, portions of ear-surround cushion 304 seal against the head of the user, so that each physiological sensor 110 in an earcup 301 make contact with a surface of a portion of a head of the user. Thus, any physiological sensor 110 described herein that generates a sensor output via contact with a portion of a body of a user can be incorporated as shown into headphone system 300. It is noted that headphone system 300 is well-suited to include a first plurality 310 of EEG sensors configured to contact a first surface of a first hemisphere of the head of the user and a second plurality 320 of EEG sensors configured to contact a second surface of a second hemisphere of the head of the user, wherein the first hemisphere and the second hemisphere are opposing hemispheres.

In some embodiments, daydream-aware information recovery system 100 is implemented in an ear-mounted device, such as an earbud system, an earpiece, or a hearable computing device. One such embodiment is illustrated in FIG. 4. FIG. 4 is a schematic diagram illustrating an ear-mounted device 400 that includes daydream-aware information recovery system 100, according to various embodiments. Ear-mounted device 400 includes, without limitation, a left earbud 401 and a right earbud 402, each coupled to a plug assembly 420 via a wired connection 403. Alternatively, left earbud 401 and/or right earbud 402 may be configured as a wireless earbud, a wireless earpiece, or a hearable computing device.

In the embodiment illustrated in FIG. 4, ear-mounted device 400 may further include user interface module 120, which may be incorporated into a volume control module coupled to left earbud 401, right earbud 402, and plug assembly 420 as shown. Ear-mounted device 400 further includes physiological sensors 110 disposed on one or more surfaces of left earbud 401 and right earbud 402. Thus, when a user has inserted left earbud 401 and right earbud 402, physiological sensors 110 are positioned in contact with respective locations within an ear canal of the user and can generate accurate sensor output, such as physiological information associated with the user.

In the embodiment illustrated in FIG. 4, physiological sensors 110 incorporated into ear-mounted device 400 are configured to contact a surface of a portion of an ear canal of the user wearing ear-mounted device 400. In other embodiments, physiological sensors 110 incorporated into ear-mounted device 400 may be configured to contact any other suitable surface of a head of a user, such as the outer ear, portions of the head of the user proximate the outer ear, a portion of the body of the user in contact with user interface module 120 and/or wired connection 403, etc. Thus, one or more of physiological sensors 110 incorporated into ear-mounted device 400 may be disposed within a component of ear-mounted device 400 that is separate from left earbud 401 and right earbud 402.

In some embodiments, daydream-aware information recovery system 100 is implemented in any other wearable computing device, such as a pair of smart glasses, a smart watch, and/or a smart ring. In such embodiments, physiological sensors 110 may be disposed on one or more surfaces of the user, and may be polled wirelessly by daydream-aware information recovery system 100. Thus, in such embodiments, measurements such as EEG, skin conductance, and/or skin temperature can be measured. In the case of smart glasses, physiological sensors 110 may be disposed on one or more surfaces of the smart glasses configured to contact a surface of a head of a user. Alternatively or additionally, in some embodiments, physiological sensors 110 may be disposed on one or more surfaces of the smart glasses that face a pupil of the user. Thus, in such embodiments, pupillometry measurements can be performed. Alternatively or additionally, in some embodiments, physiological sensors 110 may be included in a computing device external to daydream-aware information recovery system 100, such as a smartphone, an electronic tablet, and/or a head-mounted display such as an augmented reality/virtual reality/extended reality headset. In such embodiments, user-facing cameras included in such computing devices can be employed to perform pupillometry measurements, particularly when such computing devices are configured with Lidar and/or radar sensors and/or eye motion detection software. Further in some embodiments, physiological sensors 110 included in a computing device external to daydream-aware information recovery system 100 can facilitate daydreaming detection based at least in part on eye motion detection. For example, detection of eye gaze of user 102 being directed to (or away from) a specific location, as detected by physiological sensors 110, can indicate that user 102 has entered a daydream state. In another example, detection of eye vergence on the part of user 102 (e.g., parallel gaze, or looking into nothing), as detected by physiological sensors 110, can indicate that user 102 has entered a daydream state.

Figure 5:
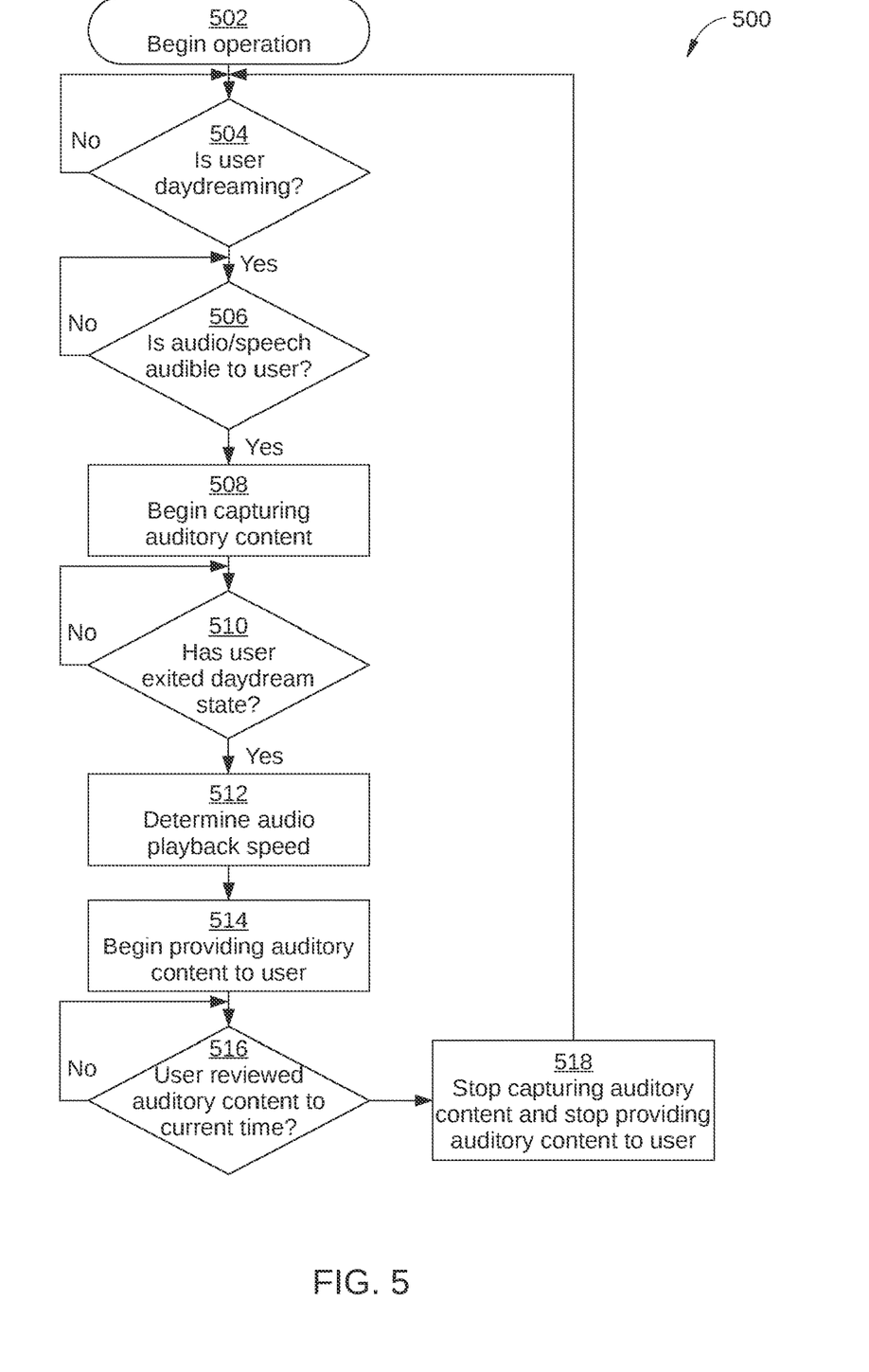
FIG. 5 sets forth a flowchart of method steps for information recovery based on detection of a daydream state experienced by a user, according to various embodiments.

FIG. 5 sets forth a flowchart of method steps for information recovery based on detection of a daydream state experienced by user 102, according to various embodiments. Although the method steps are described with respect to the systems of FIGS. 1-4, any system configured to perform the method steps, in any order, falls within the scope of the various embodiments.

As shown, a method 500 begins at step 502, in which daydream-aware information recovery system 100 begins operation. In some embodiments, daydream-aware information recovery system 100 begins operation whenever worn by user 102. In other embodiments, daydream-aware information recovery system 100 begins operation when user 102 performs a suitable input via user interface module 120 to activate daydream-aware information recovery system 100.

In step 504, information recovery controller 130 determines whether user 102 is daydreaming, based on one or more sensor outputs received from physiological sensors 110. If information recovery controller 130 determines that user 102 is not daydreaming, method 500 returns to step 504; if information recovery controller 130 determines that user 102 is daydreaming, method 500 proceeds to step 506. In some embodiments, information recovery controller 130 makes such a determination via daydream detection module 210 and the sensor outputs received from daydream-aware information recovery system 100.

In some embodiments, in step 506, information recovery controller 130 determines whether auditory content is currently audible to user 102. If information recovery controller 130 determines that auditory content is not audible to user 102, method 500 returns to step 506; if information recovery controller 130 determines that auditory content is audible to user 102, method 500 proceeds to step 508.

In other embodiments, in step 506, information recovery controller 130 determines whether auditory content that specifically includes speech is currently audible to user 102. In such embodiments, if speech or speech-containing auditory content is not detected by information recovery controller 130, method 500 returns to step 506; if speech or speech-containing auditory content is detected by information recovery controller 130, method 500 proceeds to step 508. In some embodiments, information recovery controller 130 may employ voice classification module 220 to detect speech or speech-containing auditory content in the auditory content captured by the one or more audio input devices 140.

In step 508, information recovery controller 130 begins capturing auditory content received via audio input device(s) 140. In some embodiments, information recovery controller 130 records the auditory content for subsequent playback to user 102. In such embodiments, one or more audio files may be generated for playback to user 102, and the auditory content recorded in this way may be substantially similar to the auditory content received via audio input device(s) 140. In some embodiments, information recovery controller 130 may further employ audio output processing module 160 to determine and implement a faster playback speed for the audio file(s) stored by information recovery controller 130.

In some embodiments, a representation of the auditory content captured by audio input device(s) 140 is generated that may be significantly modified from the auditory content captured via audio input device(s) 140. In some embodiments, information recovery controller 130 begins recording the auditory content, modifies the modality of the auditory content to a different modality, then stores the auditory content in the different modality for subsequent provision to user 102. In some embodiments, information recovery controller 130 employs audio input processing module 230 to perform speech clarification on the auditory content, employs speech-to-text module 240 to perform a speech-to-text-operation on at least a portion of the auditory content (such as the portion of the auditory content determined to be speech), and/or stores or otherwise records a text file of the text for subsequent provision to user 102. Thus, the text file captures a portion of the auditory content even though the text file is a different modality than the auditory content received by audio input device(s) 140. The auditory content captured by the text file can be subsequently provided to user 102 as an audio message (generated in step 522 below) that is played back once user 102 has exited the daydream state. Alternatively or additionally, the auditory content captured by the text file can be subsequently provided to user 102 as a text-based message, for example via transmission to a computing device associated with user 102. Examples of such a computing device include a smart watch, some other wearable computing device, a smartphone, an electronic tablet, a laptop computer, an e-mail server that is associated with an e-mail account of user 102, and/or the like.

In step 510, information recovery controller 130 determines whether user 102 has exited the current daydream state, based on one or more sensor outputs received from physiological sensors 110. If information recovery controller 130 determines that user 102 has not exited the current daydream state, method 500 returns to step 510 and information recovery controller 130 continues capturing auditory content; if information recovery controller 130 determines that user 102 has exited the current daydream state, method 500 proceeds to step 512.

In step 512, information recovery controller 130 determines an audio playback speed, for example based on a duration of the just completed daydreaming session and/or on a user preference for playback speed associated with user 102. In some embodiments, information recovery controller 130 employs audio output processing module 260 to determine the audio playback speed.

In step 514, information recovery controller 130 begins providing auditory content that is based on the auditory content captured in step 508. In some embodiments, in step 514, information recovery controller 130 begins playback of an audio file that is based on the auditory content captured in step 508. In some embodiments, the audio file is a recording of such auditory content.

In some embodiments, the audio file is a representation of such auditory content, such as a synthesized voice that is rendered based on a text file that is in turn based on the auditory content captured in step 508. In such embodiments, information recovery controller 130 converts a text file generated in step 508 to an audio file. In such embodiments, information recovery controller 130 may employ text-to-speech module 250 to synthesize speech generated by a speech-to-text operation performed in step 508. In some embodiments, information recovery controller 130 stores or otherwise records the audio file of the synthesized speech for subsequent playback to user 102. In such embodiments, auditory content missed by user 102 and included in the audio file of synthesized speech is condensed speech, in which pauses and extraneous sounds are not provided to user 102. Alternatively or additionally, in some embodiments, auditory content missed by user 102 and included in the audio file of synthesized speech is summarized. Consequently, in such an embodiment, user 102 can catch up on missed auditory content more quickly via playback of the condensed speech.

Alternatively or additionally, in some embodiments, the auditory content captured in step 508 is provided to user 102 via a text-based message. In such embodiments, the text-based message includes text generated in step 508 by a speech-to-text process, for example by speech-to-text module 240.

In step 516, information recovery controller 130 determines whether user 102 has reviewed auditory content up to the current time. That is, information recovery controller 130 determines whether user 102 has reviewed auditory content captured by information recovery controller 130 up to the present time. If user 102 is not caught up to the present time, method 500 returns to step 516; if user 102 is caught up to the present time, method 500 proceeds to step 518. It is noted that in the embodiment illustrated in FIG. 5, information recovery controller 130 continues to capture auditory content after determining that user 102 has exited the current daydream state.

In step 518, information recovery controller 130 stops capturing auditory content from the environment surrounding user 102 and stops audio playback of captured auditory content. Method 500 then returns to step 502.

Figure 6:
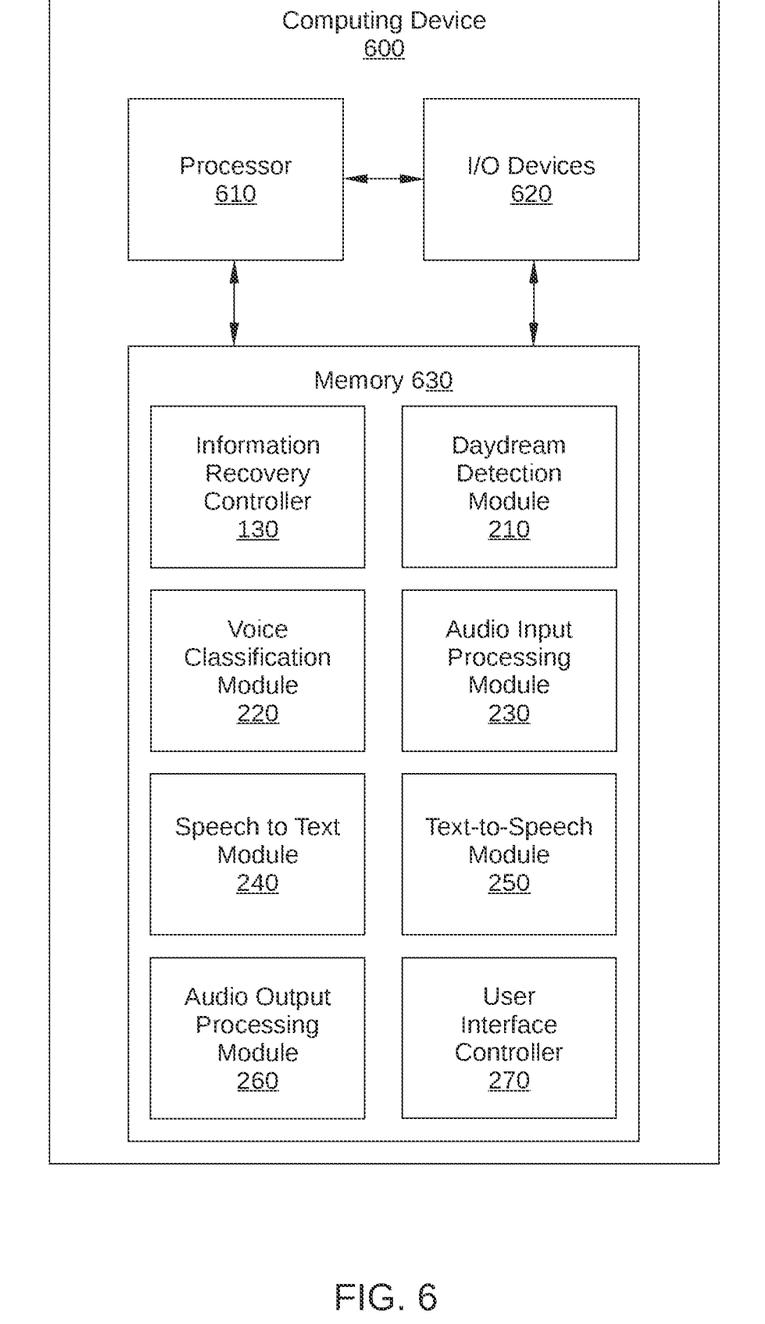
FIG. 6 is an illustration of a computing device, according to various embodiments.

FIG. 6 is an illustration of a computing device 600, according to various embodiments. Computing device 600 is configured to implement at least one aspect of the present disclosure described herein. Computing device 600 may be any type of device capable of executing application programs including, without limitation, instructions associated with information recovery controller 130, daydream detection module 210, voice classification module 220, audio input processing module 230, speech-to-text module 240, text-to-speech module 250, audio output processing module 260, and/or user interface controller 270. For example, and without limitation, computing device 600 may be an electronic tablet, a smartphone, a laptop computer, a wearable device, etc. Alternatively, computing device 600 may be implemented as a stand-alone chip, such as a microprocessor, or as part of a more comprehensive solution that is implemented as an application-specific integrated circuit (ASIC), a system-on-a-chip (SoC), and so forth. Generally, computing device 600 may be configured to coordinate the overall operation of a computer-based system, such as daydream-aware information recovery system 100. In other embodiments, computing device 600 may be coupled to, but separate from such a computer-based system. In such embodiments, the computer-based system may include a separate processor that transmits data to computing device 600, and may be included in a consumer electronic device, such as a personal computer, smartphone, or headphone-based device. As shown, computing device 600 includes, without limitation, a processor 610, input/output (I/O) devices 620, and a memory 630. Furthermore, in addition to the modules residing locally on computing device 600, one or more specific computing-intensive modules may be implemented as cloud services. For example, speech-to-text 240 module and/or text-to-speech 250 module are modules that may be advantageously implemented in the cloud. In one such embodiment, raw audio information may be transmitted wirelessly from audio input processing module 230 to a cloud-based speech-to-text 240 module, which then connects to a cloud-based text-to-speech 250 module. In the embodiment, text-to-speech 250 module may then send a text file back to be outputted locally by audio output processing module 260. In an alternative embodiment, speech-to-text 240 module is implemented in the cloud and text-to-speech 250 module is not. In another alternative embodiment, text-to-speech 250 module is implemented in the cloud speech-to-text 240 module is not.

Processor 610 may be implemented as a central processing unit (CPU), a graphics processing unit (GPU), an application-specific integrated circuit (ASIC), a field programmable gate array (FPGA), any other type of processing unit, or a combination of different processing units. In general, processor 610 may be any technically feasible hardware unit capable of processing data and/or executing software applications to facilitate operation of daydream-aware information recovery system 100, as described herein. Among other things, and without limitation, processor 610 may be configured to execute instructions associated with information recovery controller 130, daydream detection module 210, voice classification module 220, audio input processing module 230, speech-to-text module 240, text-to-speech module 250, audio output processing module 260, and/or user interface controller 270.

Memory 630 may include a random access memory (RAM) module, a flash memory unit, or any other type of memory unit or combination thereof, and may include a single memory module or a collection of memory modules. As shown, in some embodiments, some or all of information recovery controller 130, daydream detection module 210, voice classification module 220, audio input processing module 230, speech-to-text module 240, text-to-speech module 250, audio output processing module 260, and/or user interface controller 270 may reside in memory 630 during operation.

I/O devices 620 include at least one device capable of receiving input, such as a keyboard, a mouse, a touch-sensitive screen, a microphone (such as an audio input device 140) and so forth, as well as at least one device capable of providing output, such as a display screen, loudspeakers (including a loudspeaker associated with audio output devices 150), and/or the like. The display screen may be incorporated in daydream-aware information recovery system 100 or may be external to daydream-aware information recovery system 100, such as a computer monitor, a video display screen, a display apparatus incorporated into a separate hand held device, or any other technically feasible display screen.

In sum, a daydream-aware information recovery system is configured to determine that a user has entered a daydreaming state, capture auditory content from the surroundings of the user, and provide the captured auditory content to the user at a suitable time, such as after the user has finished daydreaming. The captured auditory content may be modified to facilitate review by the user and, in some embodiments, may be converted to a text-based message. Physiological sensors included in a wearable device monitor the user and enable the daydream-aware information recovery system to determine that the user has entered or exited a daydreaming state.

At least one technological improvement of the disclosed embodiments is that a user is free to enjoy the benefits of having a daydream session or other spontaneous, self-directed thoughts and associations without missing external auditory experiences or content that is audible to the user during the daydream session. Another technological improvement of the disclosed embodiments is that such external auditory experiences and/or content can be provided to the user in a different modality and/or played back at a more convenient speed. These technical advantages provide one or more technological advancements over prior art approaches.

1. In some embodiments, a system comprises: a sensing module configured to collect physiological information from a user; an audio input device configured to capture auditory content that is in an environment proximate the user; and one or more processors configured to: determine that a user has entered a state of inwardly focused attention based on first physiological information collected from the user; and in response, record the auditory content captured by the audio input device.

2. The system of clause 1, wherein: the system further comprises an audio output device configured to deliver the recorded auditory content to the user; and the one or more processors are further configured to: determine that the user has exited the state of inwardly focused attention based on second physiological information collected from the user; and cause the audio output device to playback the recorded auditory content to the user.

3. The system of clauses 1 or 2, further comprising a head-worn component, wherein the audio output device is disposed in the head-worn component.

4. The system of any of clauses 1-3, wherein the one or more processors are further configured to modify the recorded auditory content after recording.

5. The system of any of clauses 1-4, wherein the one or more processors are configured to modify the captured auditory content by at least one of performing a signal processing operation on the captured auditory content, changing a speed of playback of the captured auditory content, or changing the captured auditory content to a different modality of content.

6. The system of any of clauses 1-5, wherein the one or more processors are further configured to change the speed of playback of the captured auditory content based on at least one of a user preference or a duration of a time interval during which the auditory content is captured.

7. The system of any of clauses 1-6, wherein the sensing module is configured to collect physiological information from a group consisting of an electroencephalographic measurement, an electrodermal activity measurement, a skin temperature measurement, a pupillometry measurement, a reflective photosensing measurement, and an inertial measurement unit.

8. The system of any of clauses 1-7, further comprising a head-worn component, wherein at least one sensor of the sensing module is disposed in the head-worn component.

9. The system of any of clauses 1-8, wherein the one or more processors are further configured to: prior to causing the audio input device to capture the auditory content, determine there is audible speech content in the environment proximate the user; and based on the audible speech content, enable capturing of the auditory content.

10. A method, comprising: collecting first physiological information with a sensor included in a head-worn device that is worn by the user; capturing auditory content that is in an environment proximate the user via an audio input device included in the head-worn device; determining that the user has entered a state of inwardly focused attention based on the first physiological information; and in response, recording the auditory content captured by the audio input device.

11. The method of clause 10, further comprising: determining that the user has exited the state of inwardly focused attention based on second physiological information collected from the user with the sensor; and causing an audio output device included in the head-worn device to playback the recorded auditory content to the user.

12. The method of clauses 10 or 11, wherein the audio output device is further configured to playback the recorded auditory content to the user privately.

13. The method of any of clauses 10-12, further comprising modifying the recorded auditory content.

14. The method of any of clauses 10-13, further comprising modifying the captured auditory content by at least one of performing a signal processing operation on the captured auditory content, changing a speed of playback of the captured auditory content, or changing the captured auditory content to a different modality of content.

15. The method of any of clauses 10-14, wherein the different modality of content comprises at least one of a text-based message for transmission to a computing device associated with the user, an audio message for transmission to the computing device, or an audio message for playback to the user that is based on a text-based message generated from the captured auditory content.

16. The method of any of clauses 10-15, further comprising transmitting at least one of the text-based message to the computing device or the audio message to the computing device.

17. The method of any of clauses 10-16, further comprising changing the speed of playback of the captured auditory content based on at least one of a user preference or a duration of a time interval during which the auditory content is captured.

18. One or more non-transitory computer readable media storing instructions that, when executed by one or more processors, cause the one or more processors to perform the steps of: collecting first physiological information with a sensor included in a head-worn device that is worn by the user; capturing auditory content that is in an environment proximate the user via an audio input device included in the head-worn device; determining that the user has entered a state of inwardly focused attention based on the first physiological information; and in response, recording the auditory content captured by the audio input device.

19. The one or more non-transitory computer readable media of clause 18, wherein: determining that the user has exited the state of inwardly focused attention based on second physiological information collected from the user with the sensor; and causing an audio output device included in the head-worn device to playback the recorded auditory content to the user.

20. The one or more non-transitory computer readable media of clauses 18 or 19, wherein the instructions, when executed by the one or more processors, cause the one or more processors to perform the step of modifying the recorded auditory content after recording.

Any and all combinations of any of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module" or "system." In addition, any hardware and/or software technique, process, function, component, engine, module, or system described in the present disclosure may be implemented as a circuit or set of circuits. Furthermore, aspects of the present disclosure may take the form of a computer program product embodied in at least one computer readable medium having computer readable program code embodied thereon.

Any combination of at least one computer readable medium may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having at least one wire, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors or gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises at least one executable instruction for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A system, comprising:
a sensing module configured to collect physiological information from a user;
an audio input device configured to capture auditory content that is in an environment proximate the user; and
one or more processors configured to:
determine there is audible speech content in the auditory content,
determine that the user has entered a daydreaming state based on first physiological information collected from the user; and
in response to determining that the user has entered the daydreaming state and that there is audible speech content in the auditory content, record the auditory content captured by the audio input device.

2. The system of claim 1, wherein:
the system further comprises an audio output device configured to deliver the recorded auditory content to the user; and
the one or more processors are further configured to:
determine that the user has exited the daydreaming state based on second physiological information collected from the user; and
cause the audio output device to playback the recorded auditory content to the user.

3. The system of claim 2, further comprising a head-worn component, wherein the audio output device is disposed in the head-worn component.

4. The system of claim 1, wherein the one or more processors are further configured to modify the recorded auditory content after recording.

5. The system of claim 1, wherein the one or more processors are further configured to modify the captured auditory content by changing the captured auditory content to a different modality of content.

6. The system of claim 1, wherein the one or more processors are further configured to change speed of playback of the recorded auditory content based on a duration of a time interval during which the auditory content is recorded.

7. The system of claim 1, wherein the sensing module is configured to collect physiological information from a group consisting of an electroencephalographic measurement, an electrodermal activity measurement, a skin temperature measurement, a pupillometry measurement, a reflective photosensing measurement, and an inertial measurement unit.

8. The system of claim 1, further comprising a head-worn component, wherein at least one sensor of the sensing module is disposed in the head-worn component.

9. A method, comprising:
collecting first physiological information with a sensor included in a head-worn device that is worn by a user;
capturing auditory content that is in an environment proximate the user via an audio input device included in the head-worn device;
determining there is audible speech content in the auditory content;
determining that the user has entered a daydreaming state based on the first physiological information; and
in response to determining that the user has entered the daydreaming state and that there is audible speech content in the auditory content, recording the auditory content captured by the audio input device.

10. The method of claim 9, further comprising:
    determining that the user has exited the daydreaming state based on second physiological information collected from the user with the sensor; and
    causing an audio output device included in the head-worn device to playback the recorded auditory content to the user.

11. The method of claim 10, wherein the audio output device is further configured to playback the recorded auditory content to the user privately.

12. The method of claim 10, further comprising modifying the recorded auditory content.

13. The method of claim 12, further comprising modifying the captured auditory content by changing the captured auditory content to a different modality of content.

14. The method of claim 13, wherein the different modality of content comprises at least one of:
    a text-based message for transmission to a computing device associated with the user,
    an audio message for transmission to the computing device, or
    an audio message for playback to the user that is based on a text-based message generated from the captured auditory content.

15. The method of claim 14, further comprising transmitting at least one of the text-based message to the computing device or the audio message to the computing device.

16. The method of claim 9, further comprising changing a speed of playback of the recorded auditory content based on a duration of a time interval during which the auditory content is recorded.

17. One or more non-transitory computer readable media storing instructions that, when executed by one or more processors, cause the one or more processors to perform the steps of:
    collecting first physiological information with a sensor included in a head-worn device that is worn by a user;
    capturing auditory content that is in an environment proximate the user via an audio input device included in the head-worn device;
    determining there is audible speech content in the auditory content;
    determining that the user has entered a daydreaming state based on the first physiological information; and
    in response to determining that the user has entered the daydreaming state and that there is audible speech content in the auditory content, recording the auditory content captured by the audio input device.

18. The one or more non-transitory computer readable media of claim 17, wherein:
    determining that the user has exited the daydreaming state based on second physiological information collected from the user with the sensor; and
    causing an audio output device included in the head-worn device to playback the recorded auditory content to the user.

19. The one or more non-transitory computer readable media of claim 17, wherein the instructions, when executed by the one or more processors, cause the one or more processors to perform the step of modifying the recorded auditory content after recording.

* * * * *